United States Patent [19]

Thor et al.

[11] Patent Number: 5,411,705
[45] Date of Patent: May 2, 1995

[54] COMBINED CARDIOTOMY AND VENOUS BLOOD RESERVOIR

[75] Inventors: Eric J. Thor, Columbia Heights; Kevin D. McIntosh, Albertville; Bruce R. Jones; Jeremy D. Dando, both of Plymouth, all of Minn.

[73] Assignee: Avecor Cardiovascular Inc., Plymouth, Minn.

[21] Appl. No.: 182,731

[22] Filed: Jan. 14, 1994

[51] Int. Cl.⁶ .................. A61M 1/14; A61M 1/34; B01D 27/00
[52] U.S. Cl. .................. 422/45; 128/DIG. 3; 210/436; 422/44; 422/46; 422/47; 604/4; 604/126; 604/122; 604/317
[58] Field of Search .................. 128/DIG. 3; 210/436; 422/44–47, 101; 604/4–6, 126, 122, 317, 324

[56] References Cited

U.S. PATENT DOCUMENTS

| Re. 32,711 | 7/1988 | Dickens et al. | 210/448 |
|---|---|---|---|
| 3,507,395 | 4/1970 | Bentley | 604/129 X |
| 3,701,433 | 10/1972 | Krakauer et al. | 210/436 |
| 3,742,934 | 7/1973 | Holbrook et al. | 604/319 X |
| 3,768,653 | 10/1973 | Brumfield | 422/45 X |
| 3,993,461 | 11/1976 | Leonard et al. | 210/436 X |
| 4,054,523 | 10/1977 | Ingenito et al. | 210/436 X |
| 4,157,965 | 6/1979 | Raible | 210/446 X |
| 4,164,468 | 8/1979 | Raible | 210/436 X |
| 4,208,193 | 6/1980 | Munsch et al. | 210/436 X |
| 4,422,939 | 12/1983 | Sharp et al. | 210/445 |
| 4,440,723 | 4/1984 | Gordon | 422/47 |
| 4,443,220 | 4/1984 | Hauer et al. | 604/4 X |
| 4,490,331 | 10/1984 | Steg, Jr. | 422/46 |
| 4,517,090 | 5/1985 | Kersten et al. | 604/4 X |
| 4,568,367 | 2/1986 | Gremel et al. | 422/47 X |
| 4,585,056 | 4/1986 | Oscarsson | 422/46 X |
| 4,642,089 | 2/1987 | Zupkas et al. | 604/4 |
| 4,662,906 | 5/1987 | Matkovich et al. | 604/126 X |
| 4,664,682 | 5/1987 | Monzen | 604/406 |
| 4,668,394 | 5/1987 | Badolato et al. | 604/5 X |
| 4,705,497 | 11/1987 | Shitaokoshi et al. | 604/4 |
| 4,737,139 | 4/1988 | Zupkas et al. | 604/4 |
| 4,743,371 | 5/1988 | Servas et al. | 210/188 |
| 4,747,844 | 5/1988 | Elliott | 604/319 |
| 4,756,705 | 7/1988 | Beijbom et al. | 604/4 |
| 4,822,346 | 4/1989 | Elliott | 604/319 |
| 4,846,800 | 7/1989 | Ouriel et al. | 604/319 X |
| 4,876,066 | 10/1989 | Bringham et al. | 422/46 |
| 4,919,802 | 4/1990 | Katsura | 210/436 X |
| 4,923,438 | 5/1990 | Vasconcellos et al. | 604/4 |
| 4,936,759 | 6/1990 | Clausen et al. | 128/DIG. 3 X |
| 5,034,188 | 7/1991 | Nakanishi et al. | 422/46 |
| 5,039,430 | 8/1991 | Corey, Jr. | 604/4 X |
| 5,039,482 | 8/1991 | Panzani et al. | 422/46 |
| 5,043,140 | 8/1991 | Combs | 422/46 |
| 5,049,146 | 9/1991 | Bringham et al. | 604/4 |
| 5,087,250 | 2/1992 | Lichte et al. | 604/4 X |
| 5,112,480 | 5/1992 | Hukasawa | 422/45 X |
| 5,120,302 | 6/1992 | Vescovini et al. | 604/4 |
| 5,120,501 | 6/1992 | Mathewson et al. | 422/46 |
| 5,127,900 | 7/1992 | Schickling et al. | 604/4 |
| 5,149,318 | 9/1992 | Lindsay | 604/4 |
| 5,160,332 | 11/1992 | Nomura | 604/122 X |
| 5,167,921 | 12/1992 | Gordon | 422/45 |
| 5,192,439 | 3/1993 | Roth et al. | 604/403 X |

*Primary Examiner*—James C. Housel
*Assistant Examiner*—Arlen Soderquist
*Attorney, Agent, or Firm*—Popovich & Wiles

[57] ABSTRACT

A reservoir for use in an extracorporeal blood circuit including a rigid shell forming an enclosed reservoir. A filter unit divides the reservoir into an inlet chamber and outlet chamber. Cardiotomy blood filtering and defoaming means and venous blood filtering and defoaming means are located within the inlet chamber.

26 Claims, 8 Drawing Sheets

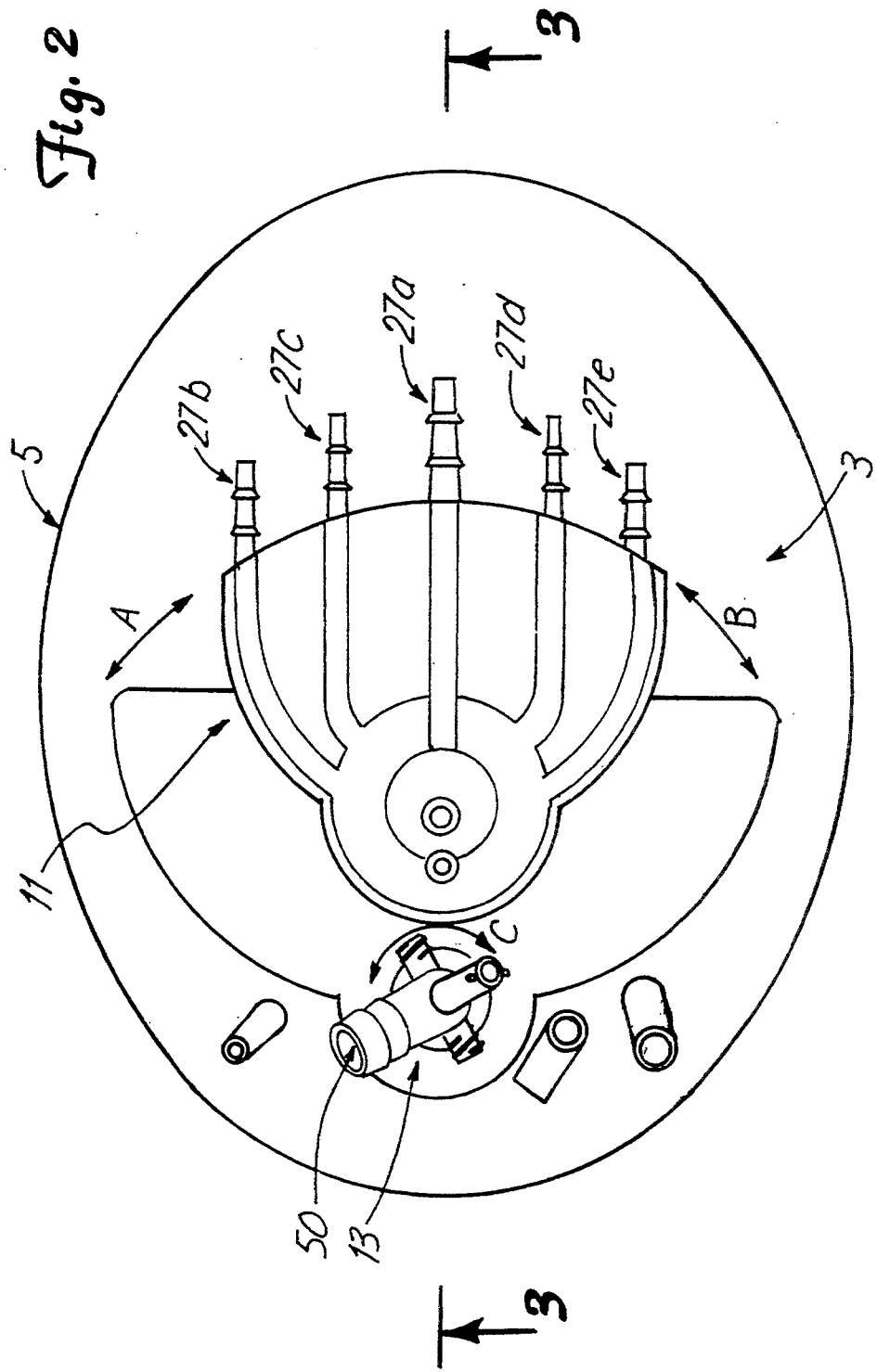

COMBINED CARDIOTOMY AND VENOUS BLOOD RESERVOIR

FIELD OF THE INVENTION

The present invention provides a combined cardiotomy and venous blood reservoir for use in an extracorporeal blood circuit commonly used during various surgical procedures, such as open-heart surgery.

BACKGROUND OF THE INVENTION

In various surgical procedures, an extracorporeal blood circuit is created to bypass the surgery site. In a cardiopulmonary surgical procedure, a bypass circuit is created where venous blood bypasses the heart and is reintroduced into an artery. Also, cardiotomy blood is scavenged from the surgical site, combined with the venous blood, and reintroduced into the patient. The extracorporeal bypass circuit performs numerous functions, including removing emboli and particulate matter entrained in the blood, regulating the carbon dioxide and oxygen content of the blood, and regulating the blood temperature.

In prior art extracorporeal bypass circuits, the venous blood is filtered and collected in a venous reservoir and the cardiotomy blood is filtered and collected in a hard shell cardiotomy reservoir. Examples of such devices include a venous reservoir as disclosed in U.S. Pat. No. 5,061,236 and a cardiotomy reservoir as disclosed in U.S. Pat. No. 4,743,371. Also, integrated venous/cardiotomy reservoirs are known, e.g., U.S. Pat. No. 4,642,089.

Some of these prior art reservoirs have blood flow paths that either cause blood stagnation or trap gas bubbles in the blood. Further, prior art cardiotomy reservoirs typically include a defoaming element that includes an antifoam agent to eliminate blood foam. Exposing blood to the antifoam agent continually is unnecessary. The present invention is directed to a combined venous and cardiotomy reservoir that provides a simpler and more efficient blood storage, filtration, and defoaming system for both venous and cardiotomy blood. Further, the present invention provides a blood reservoir that minimizes areas where blood may stagnate, and enhances the escape of gas emboli from the blood. Also, the present invention is configured so that blood defoaming filters treated with an antifoam agent are positioned above the standard operating fluid level of the reservoir so that blood foam contacts the defoaming filters and fluid blood contact with the filters is minimized.

SUMMARY OF THE INVENTION

According to the invention there is provided a combined venous and cardiotomy blood reservoir comprising a rigid shell having a top, a bottom, and a continuous sidewall, where the top and bottom are connected to the sidewall to form an enclosed reservoir. A filter unit having two faces and four sides is disposed within the reservoir where two of the sides are opposed and connected to the sidewall and the other two sides are opposed and connected, respectively, to the top and bottom. The filter unit divides the enclosed reservoir into an enclosed inlet chamber and an enclosed outlet chamber where the inlet chamber and outlet chamber are in fluid communication through the filter unit.

A means for cardiotomy blood filtering and defoaming is located within the inlet chamber, extending substantially from the top to the bottom of the shell. A cardiotomy blood inlet is in fluid communication with the cardiotomy blood and filtering defoaming means. A means for venous blood filtering and defoaming is located within the inlet chamber, is separate of the cardiotomy blood filtering and defoaming means, and extends substantially from the top to the bottom of the shell. A venous blood inlet is in fluid communication with the venous blood filtering and defoaming means. A blood outlet is in fluid communication with the outlet chamber for discharging venous blood and cardiotomy blood which has passed through the filter unit.

In an embodiment of the invention, the filter unit comprises a filter element and means for supporting the filter element. The filter element can be a screen, such as a polyester screen having a pore size within the range of 100 to 200 microns. Also, the cardiotomy blood filtering and defoaming means comprises a cardiotomy filter element having a top and a bottom where the cardiotomy filter element extends substantially from the top to the bottom of the shell. A first defoaming element extends from the top of the cardiotomy filter element partially toward the bottom of the cardiotomy filter element and is surrounded by the cardiotomy filter element. The cardiotomy blood filtering and defoaming means also comprises a second defoaming element extending from the top of the cardiotomy filter element partially toward the bottom of the cardiotomy filter element and surrounding the cardiotomy filter element. The cardiotomy filter element may be a depth filter, such as a polyester felt filter, having a pore size within the range of 20 to 50 microns. The first defoaming element comprises a thermally reticulated polyurethane foam having a porosity within the range of 5 to 50 pores per inch (ppi), and coated with an antifoam agent. Also, the second defoaming element comprises a thermally reticulated polyurethane foam having a porosity within the range of 5 to 50 ppi.

In an embodiment of the invention, the venous blood filtering and defoaming means comprises a cylindrical venous filter element extending substantially from the top to the bottom of the shell and a means for supporting the venous filter element. The venous filter element comprises a polyester screen having a pore size within the range of 50 to 250 microns. The venous filtering and defoaming means also includes a third defoaming element extending from the top of the shell partially toward the bottom of the shell and surrounded by the cylindrical venous filter element. The third defoaming element comprises a thermally reticulated polyurethane foam having a pore size within the range of 5 to 50 ppi, and coated with an antifoam agent. The means for supporting the venous filter comprises a cylindrical web frame having a plurality of apertures wherein the frame is surrounded by the venous filter element.

In an embodiment of the invention the combined venous and cardiotomy blood reservoir also comprises displacement means disposed within the outlet chamber for creating a uniform blood flow in the outlet chamber, displacing volume for enhancing outlet chamber blood volume measurement, and reducing air entraining vortices in the blood near the blood outlet. A substantial portion of the bottom of the shell slopes away from the top, and the outlet is located at the portion of the bottom furthest from the top. The cardiotomy blood inlet and venous blood inlet are located on the top of the shell. In other embodiments of the invention, the cardiotomy blood inlet and venous blood inlet are located on the sidewall of the shell adjacent to the top.

In an alternate embodiment of the invention, a blood reservoir comprises a rigid shell having a top, a bottom, and a continuous sidewall, where the top and bottom are connected to the sidewall to form an enclosed reservoir. A means for venous blood filtering is located within the reservoir. The venous blood filtering means comprises a cylindrical venous filter element extending substantially from the top to the bottom of the shell and means for supporting the venous filter element. The support means comprises a web frame having a plurality of apertures and surrounded by said venous filter element. The venous blood filtering means is in fluid communication with the venous blood inlet. A blood outlet is in fluid communication with the reservoir for discharging blood.

In an alternate embodiment of the invention there is an extracorporeal blood circuit comprising a combined venous and cardiotomy blood reservoir, a heat exchanger for regulating the temperature of blood comprising a heat exchanger inlet and a heat exchanger outlet, where the heat exchanger is in fluid communication with the combined venous and cardiotomy blood reservoir. A blood oxygenator for regulating the oxygen and carbon dioxide content of the blood, comprising an oxygenator blood inlet and an oxygenator blood outlet, is in fluid communication with the heat exchanger. The combined venous and cardiotomy blood reservoir comprises a rigid shell having a top, a bottom, and a continuous sidewall, where the top and bottom are connected to the sidewall to form an enclosed reservoir. A filter unit, having two faces and four sides, is disposed within the reservoir where two of the sides are opposed and connected to the sidewall and the other two of the sides are opposed and connected, respectively, to the top and bottom. The filter unit divides the enclosed reservoir into an enclosed inlet chamber and an enclosed outlet chamber where the inlet chamber and outlet chamber are in fluid communication through the filter unit. A means for cardiotomy blood filtering and defoaming is located within the inlet chamber and extends substantially from the top to the bottom of the shell. A cardiotomy blood inlet is in fluid communication with the cardiotomy blood filtering and defoaming means. A means for venous blood filtering and defoaming is located within the inlet chamber separate of the cardiotomy blood filtering and defoaming means, and extends substantially from the top to the bottom of the shell. A venous blood inlet is in fluid communication with the venous blood filtering and defoaming means. A blood outlet is in fluid communication with the outlet chamber for discharging venous blood and cardiotomy blood which has passed through the filter unit.

BRIEF DESCRIPTION OF THE DRAWINGS

FIG. 2 is a top view of the reservoir of the present invention.

DETAILED DESCRIPTION OF THE PREFERRED EMBODIMENT

Figure 1:
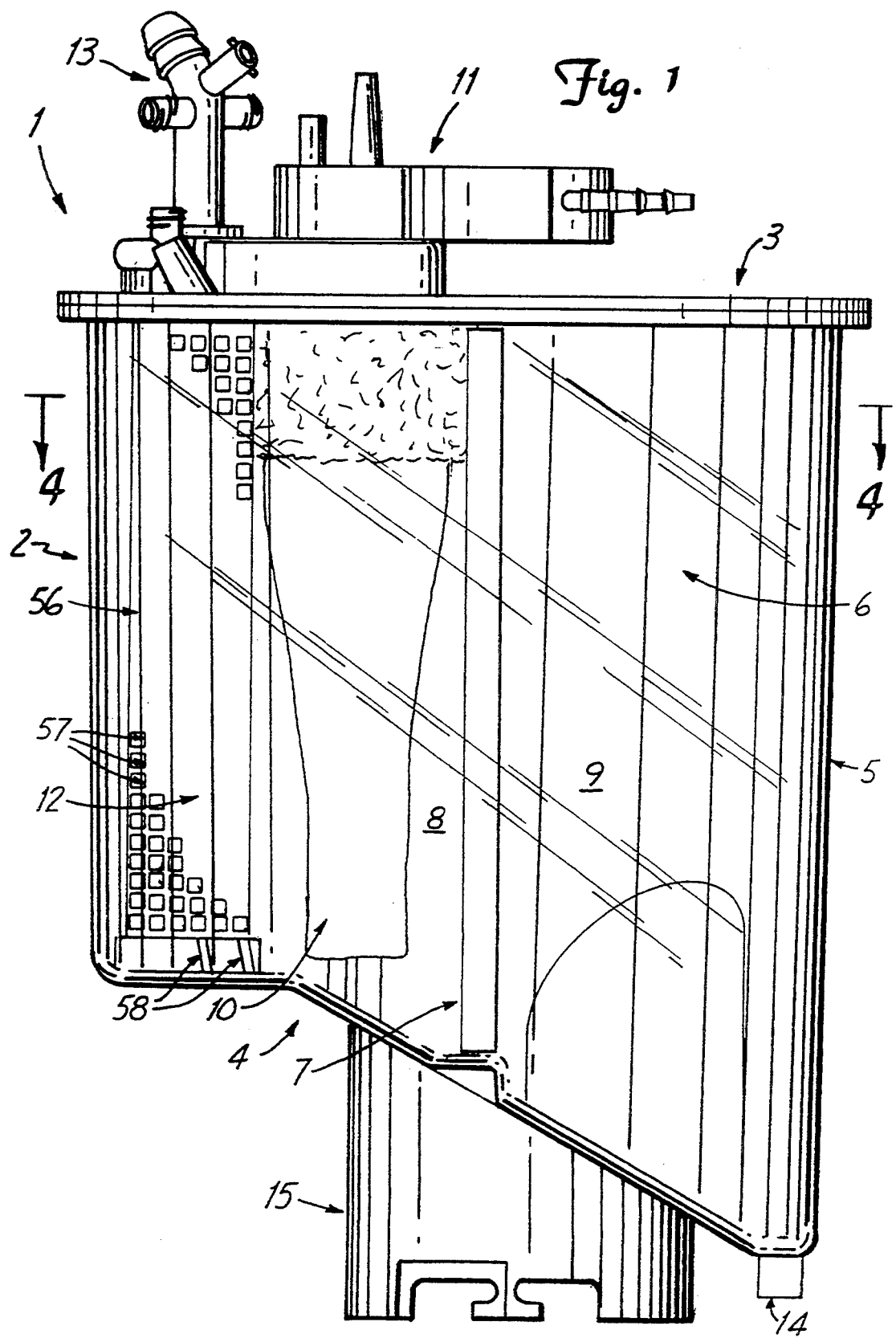
FIG. 1 is a side elevational view of the reservoir of the present invention.
Figure 1A:
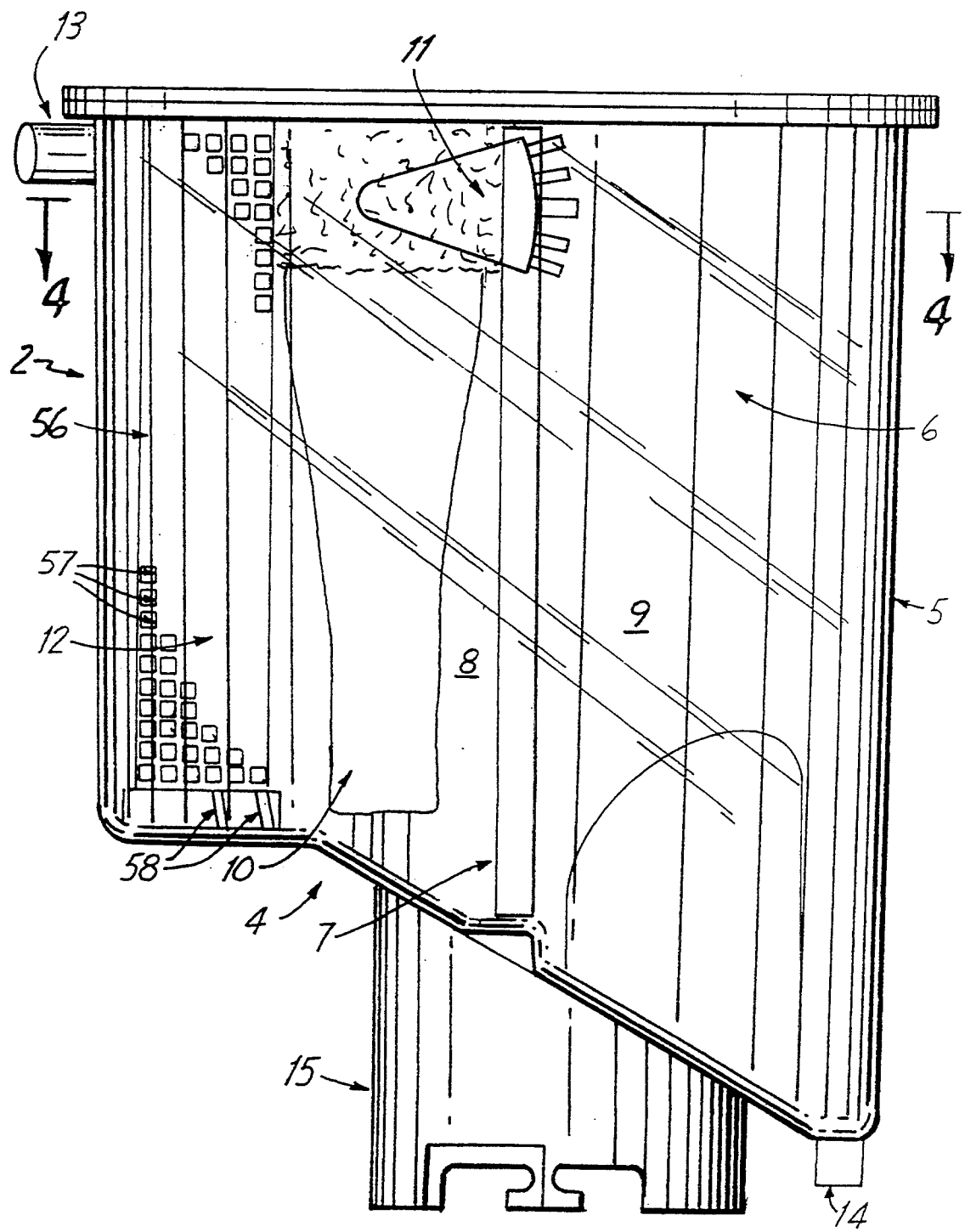
FIG. 1a is a side elevational view of an alternate embodiment of the present invention.

Referring to FIG. 1, there is shown a combined cardiotomy and venous blood reservoir 1 of the present invention. Reservoir 1 includes a rigid shell 2 having a top 3, a bottom 4 and a continuous sidewall 5 forming an enclosed reservoir 6. Enclosed reservoir 6 includes filter unit 7 that divides enclosed reservoir 6 into an enclosed inlet chamber 8 and an enclosed outlet chamber 9, wherein inlet chamber 8 and outlet chamber 9 are in fluid communication through filter unit 7. A means for cardiotomy blood filtering and defoaming 10 is disposed within inlet chamber 8 and is in fluid communication with a cardiotomy blood inlet 11. A means for venous blood filtering and defoaming 12 is also located in the inlet chamber 8, spaced from the cardiotomy blood filtering and defoaming means 10, and is in fluid communication with a venous blood inlet 13. A blood outlet 14 is in fluid communication with outlet chamber 9 for discharging combined venous and cardiotomy blood after the combined blood passes through filter unit 7. A mounting bracket 15 is optionally connected to bottom 4 for connecting reservoir 1 to a support stand or another component of the extracorporeal circuit.

Figure 3:
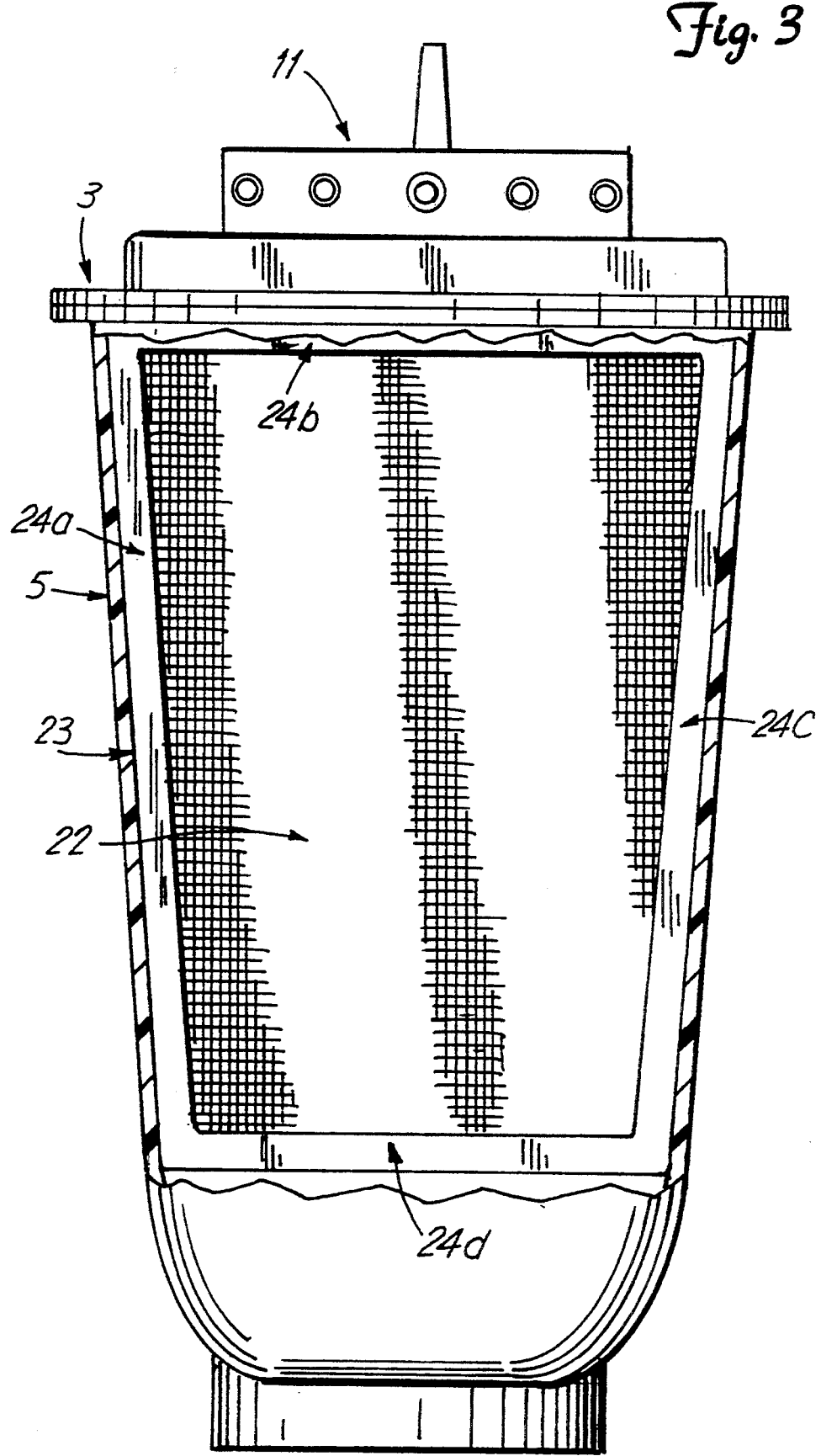
FIG. 3 is a front elevational view of the reservoir of the present invention.

Rigid shell 2 is made of molded plastic or other suitable material that does not expand or contract when shell 2 receives or discharges blood. In the preferred embodiment, hard shell 2 is made of a clear plastic so that medical personnel can observe the blood level in reservoir 1. As shown in FIG. 2, sidewall 5 has a generally elliptical cross sectional shape. As shown in FIG. 3, sidewall 5 has a slight inward taper from top 3 to bottom 4. In alternate embodiments, the cross section of sidewall 5 may be circular or have other shapes that minimize blood stagnation. Further, sidewall 5 may be cylindrical or have other shapes from top 3 to bottom 4.

Figure 4:
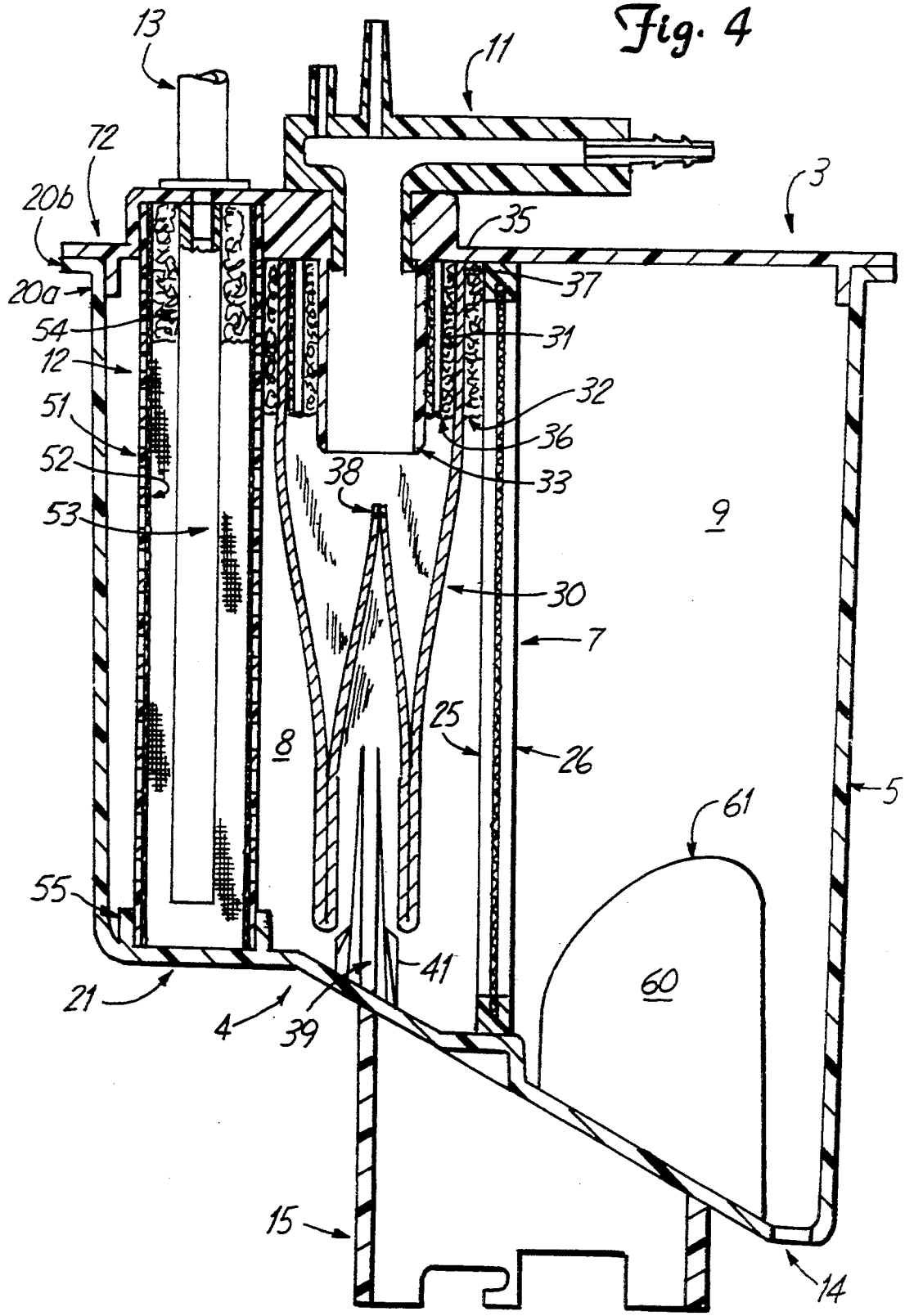
FIG. 4 is a side sectional view of the reservoir of the present invention.

In the preferred embodiment as shown in FIG. 4, sidewall 5 and bottom 4 are integrally-formed, molded plastic, while top 3 is a separate plastic lid that snap-fits onto top edge 20a of sidewall 5. Top edge 20a may also include flange 20b for an easier snap-fit. The snap-fit between top 3 and top edge 20a of sidewall 5 may be achieved by any well-known method. In alternate embodiments, top 3 may be integrally molded with or sealed to sidewall 5 by known methods.

As shown in FIG. 4, top 3 is generally planar. Bottom 4 has a planar ledge 21 supporting venous blood filtering and defoaming means 12. Ledge 21 is generally parallel to top 3, then a substantial portion of bottom 4 slopes away from top 3 to blood outlet 14 which is farthest from top 3. Therefore, blood flowing from either the cardiotomy blood or venous blood inlets 11, 13 will flow through the respective filters 10, 12, downward toward blood outlet 14, minimizing areas where blood might stagnate.

Disposed within rigid shell 2 is filter unit 7. Filter unit 7 serves primarily to remove emboli, e.g., gas bubbles and blood clots entrained in the blood, but also serves to remove particulate matter that is not trapped in filters 10 and 12. As shown in FIG. 3, filter unit 7 includes filter element 22 and means for supporting the filter element 23. In the preferred embodiment of the invention, the supporting means 23 is a generally rectangular frame of high density polyethylene or other suitable material. Frame 23 has four sides 24a, 24b, 24c, 24d. In the preferred embodiment, filter element 22 is a polyester screen molded into the frame 23. Screen 22 has an aperture size in the range of 100 to 200 microns, preferably 150 microns. Filter unit 7 is press-fit into rigid shell 2 so that opposed sides 24a, 24c are connected to sidewall 5 and opposed sides 24b, 24d are connected to top 3 and bottom 4 of the rigid shell. Filter unit 7 has a first face 25 on the inlet chamber side, and a second face 26 on the outlet chamber side. Therefore, inlet chamber 8 and outlet chamber 9 are in fluid communication through filter unit 7. In alternate embodiments of the invention, filter element 22 and supporting means 23 may be made of other suitable materials, and filter unit 7 may be fixed in place within rigid shell 2 by other suitable means.

As shown in FIG. 2, the preferred embodiment of the invention includes cardiotomy blood inlet 11 located on top 3 of reservoir 1. The cardiotomy blood inlet 11 includes a plurality of cardiotomy inlet ports 27a–e that are connected to sucker lines with pumps (not shown) that are placed at the surgical site to collect blood. In the preferred embodiment, cardiotomy inlet port 27a is ⅜" diameter, while ports 27b–e are ¼" diameter. The cardiotomy blood inlet 11 is rotatable about an axis orthogonal to top 3 as shown by arrows A and B, allowing the sucker lines to be connected to the cardiotomy inlet ports 27a–e in the most convenient and efficient manner. Cardiotomy blood flows from the cardiotomy blood inlet 11 into the means for cardiotomy blood filtering and defoaming 10. In an alternate embodiment, cardiotomy blood inlet 11 is located on sidewall 5 adjacent to top 3.

As shown in FIG. 4, the cardiotomy blood filtering and defoaming means 10 is disposed in inlet chamber 8 and extends substantially from top 3 to bottom 4. Cardiotomy blood filtering and defoaming means 10 serves to trap bone fragments, cartilage, and surgical waste collected with the cardiotomy blood at the surgical site, as well as emboli trapped in the blood. The cardiotomy blood filtering and defoaming means 10 includes cardiotomy filter element 30, first defoaming element 31, and second defoaming element 32.

In the preferred embodiment of the invention, first defoaming element 31 comprises an open cell, blood compatible, synthetic polymeric foam material to collapse blood foam into fluid blood. First defoaming element 31 is preferable formed of a thermally reticulated, polyurethane foam having a pore per inch (ppi) size in the range of 5 to 50 ppi, preferably about 10 ppi. Preferably, first defoaming element 31 is treated with a medical antifoam agent to assist defoaming. Suitable antifoam agents include silicone antifoams.

Figure 5:
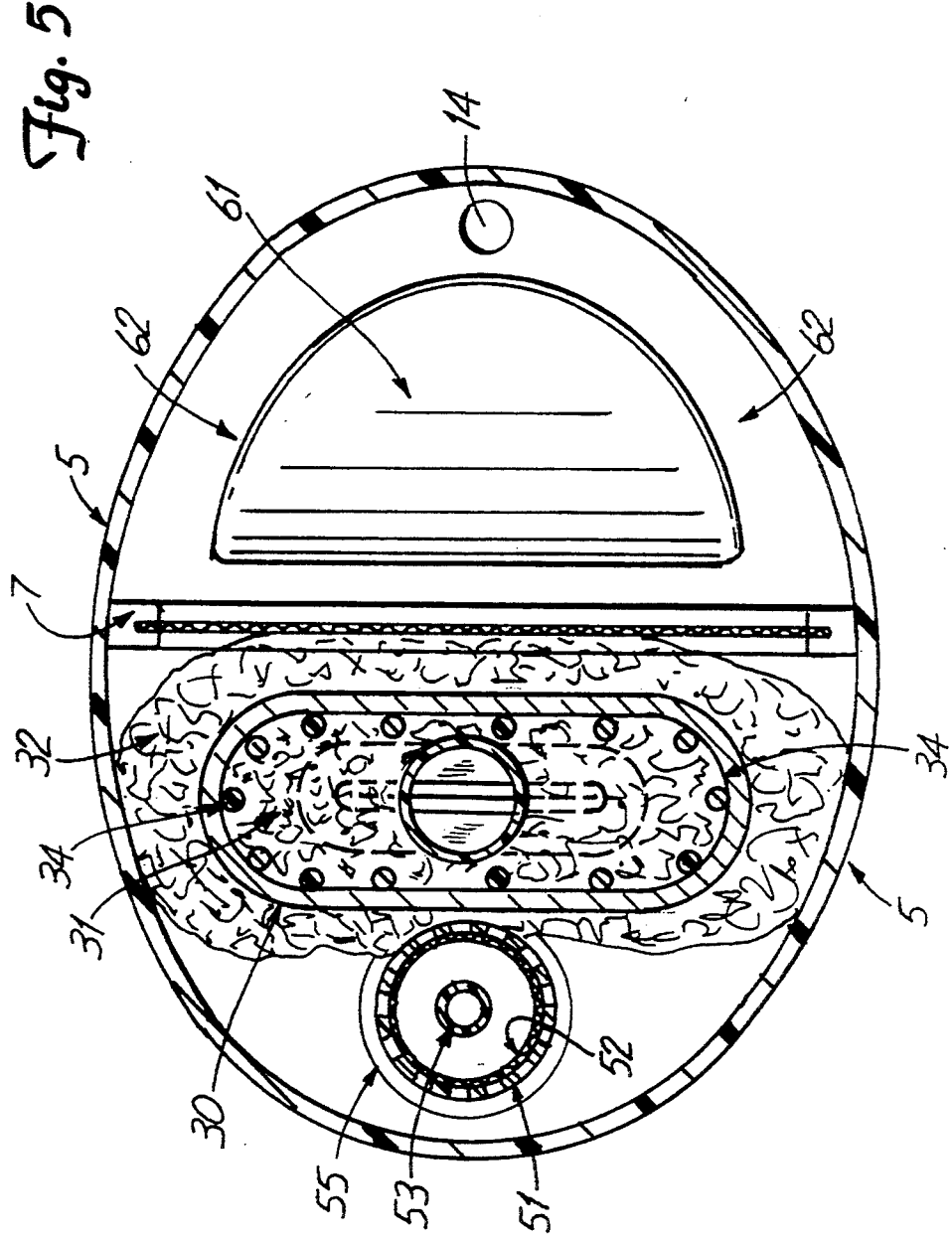
FIG. 5 is a top sectional view of the reservoir of the present invention.

First defoaming element 31 surrounds the lower extension 33 of cardiotomy blood inlet 11 adjacent top 3 and top edge 37 of filter element 30. As shown in FIG. 5, first defoaming element 31 is held in place by two fingers 34 extending downward from top 3 and filter 30. In the preferred embodiment, first defoaming element 31 has a top edge 35 adjacent to top 3, and a bottom edge 36 that extends downward from top edge 37 partially toward the bottom of filter element 30 about 1 to 3 inches, preferably 2.8 inches. Bottom edge 36 is above the standard operating fluid level of reservoir 1.

Figure 6:
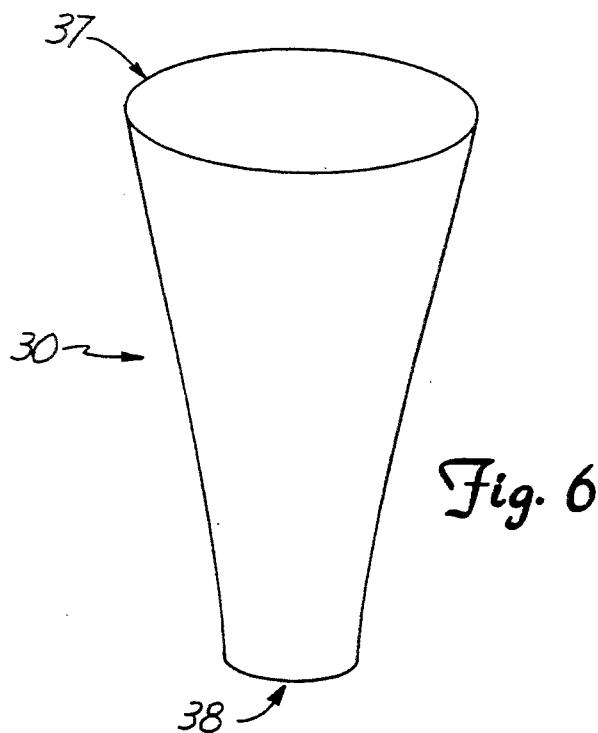
FIG. 6 is a side elevational view of the cardiotomy filter element of the present invention.

Surrounding first defoaming element 31 and extending substantially from top 3 to bottom 4 of inlet chamber 8 is cardiotomy filter element 30. Cardiotomy filter element 30 has a top edge 37 adjacent top 3 and a closed base 38. In the preferred embodiment, cardiotomy filter element 30 is a 20 micron depth filter made from Dacron ® polyester felt having a mean aperture size in the range of 20 to 50 microns, preferably 30 microns. As shown in FIG. 6, cardiotomy filter element 30 has a generally fructoconical shape, tapered from top edge 37 to the closed base 38.

As shown in FIG. 4, base 38 is folded up into filter 30, thereby maximizing the surface area of the filter while reducing the total volume required for the filter. The top edge 37 of cardiotomy filter element 30 surrounds first defoaming element 31, and fingers 34. An O-ring (not shown) fits around the upper portion of filter element 30, fixing filter 30 against fingers 34. Fingers 34 include gussets (not shown) for preventing filter 30 and the O-ring from sliding downward.

The lower portion of cardiotomy filter element 30 is supported by two filter support members 39 extending upward from bottom 4. Filter support members 39 are made of molded plastic and are stabilized by vertical fins 41. The filter support members with stabilizing fins are designed such that blood can flow out of the folded portion of filter 30 and downward toward filter unit 7. The upstream side of filter support member 39 slopes outward at bottom 4 preventing blood from stagnating on the upstream side of ribbed member 39.

Surrounding cardiotomy filter element 30 adjacent to top edge 37 is second defoaming element 32. Second defoaming element 32 is also thermally reticulated, polyurethane foam. In an alternate embodiment of the invention, this foam is treated with an antifoam agent or other medical surfactant. The pore size of the foam is within the range of 5 to 50 ppi, preferably about 30 ppi. Defoaming element 32 extends partially toward the bottom of filter element 30, about 1 to 2 inches, preferably 1.4 inches. The bottom edge of second defoaming element 32 is above the standard operating fluid level of reservoir 1.

In alternate embodiments of the invention, filter 30 and defoaming elements 31, 32 may be made of other suitable materials. Further, cardiotomy blood filtering and defoaming means 10 may not be immediately adjacent top 3 or bottom 4; however, means 10 will extend at least two-thirds of the distance between top 3 and bottom 4. Also, means 10 may have a circular or other shape extending between top 3 and bottom 4.

As shown in FIG. 2, in the preferred embodiment of the invention venous blood inlet 13 is located on top 3 of reservoir 1. The venous blood inlet 13 includes a one-half inch diameter venous inlet port 50. Venous inlet 13 is rotatable about an axis orthogonal to top 3 as shown by arrow C, allowing a venous line (not shown) to be connected to the venous inlet 13 in the most convenient and efficient manner. Venous blood flows from venous blood inlet 13 into means for venous blood filtering and defoaming 12. In an alternate embodiment, venous blood inlet 13 is located on sidewall 5 adjacent to top 3.

As shown in FIG. 4, venous blood filtering and defoaming means 12 is disposed in inlet chamber 8 separate of cardiotomy blood filtering and defoaming means 10, and extends substantially from top 3 to bottom 4 of hard shell 2. Venous blood generally does not contain bone fragments, cartilage, or surgical waste found in cardiotomy blood, but may include gas bubbles or other emboli that must be filtered out of the venous blood before it is recirculated into the patient. Venous filtering and defoaming means 12 includes cylindrical venous filter element 51 and means for supporting the venous filter element 52 extending substantially from top 3 to bottom 4 of shell 2, inlet tube 53, venous defoaming element 54, and venous stand 55.

Venous blood flows from venous inlet 13 into inlet tube 53. Inlet tube 53 is medical grade plastic tubing having, for example, a one-half inch inner diameter. Inlet tube 53 extends from venous inlet 13 at top 3 to approximately 0.1 to 0.2 inches, preferably 0.15 inches, from bottom 4 at ledge 21.

Surrounding inlet tube 53 adjacent top 3 is venous defoaming element 54. In the preferred embodiment, venous defoaming element 54 is also made of thermally reticulated, polyurethane foam having a pore size in the range of 5 to 50 ppi, preferably 30 ppi, and treated with an antifoam agent. Third defoaming element 54 extends from top 3 partially toward bottom 4 about 1 to 2 inches, preferably 1.4 inches. The bottom edge of third defoaming element 54 is above the standard operating fluid level of reservoir 1. In an alternate embodiment of the invention, third defoaming element 54 may be spaced from top 3 or include a gap or hole in the foam adjacent recirculation port 74 so that recirculated blood can flow into venous blood filtering and defoaming means 12 and downward along inlet robe 53.

Venous filter support means 52 surrounds venous defoaming element 54 and extends from top 3 to base 4. The lower portion of support means 52 fits into venous stand 55, discussed further below. As shown in FIG. 1, support means 52 has a cylindrical web frame 56 with a plurality of apertures 57.

Surrounding support means 52 is venous filter element 51. In the preferred embodiment, filter element 51 is a polyester screen having a pore size in the range of 50 to 250 microns, preferably 200 microns. Screen 51 extends from top 3 to bottom 4. Venous stand 55 surrounds the lower portion of filter element 51 and support means 52 holding venous filtering means 12 in a fixed position. Stand 55 includes aperture 58 allowing blood in the lower portion of filter element 52 to flow out of stand 55 and downward toward filter unit 7.

In alternate embodiments of the invention, venous filter element 51 and venous defoaming element 54 may be made of other suitable materials. Further, venous blood filtering and defoaming means 12 may not be immediately adjacent top 3 or bottom 4; however, means 12 will extend at least two-thirds of the distance between top 3 and bottom 4. Also, means 12 may have a circular or other shape extending between top 3 and bottom 4.

As shown in FIG. 4, displacement means 60 is disposed within outlet chamber 9. In the preferred embodiment of the invention, displacement means 60 is molded into bottom 4. Displacement means 60 has a generally rounded top surface 61, and a generally elliptically curved lateral surface 62. After blood flows through filter unit 7, displacement means 60 creates a uniform blood flow in outlet chamber 9 by forcing the blood to flow over top surface 61 or around lateral surface 62. Also, the channel formed between lateral surface 62 of displacement means 60 and sidewall 5 further serves to reduce the formation of vortices in the blood near outlet 14. Finally, displacement means 60 displaces the volume of outlet chamber 9 for enhancing blood volume measurement in outlet chamber 9.

As shown in FIG. 4, blood outlet 14 is disposed in outlet chamber 9 at the lowermost portion of bottom 4. In the preferred embodiment of the invention, blood outlet 14 has a $\frac{3}{8}''$ diameter opening.

Figure 7:
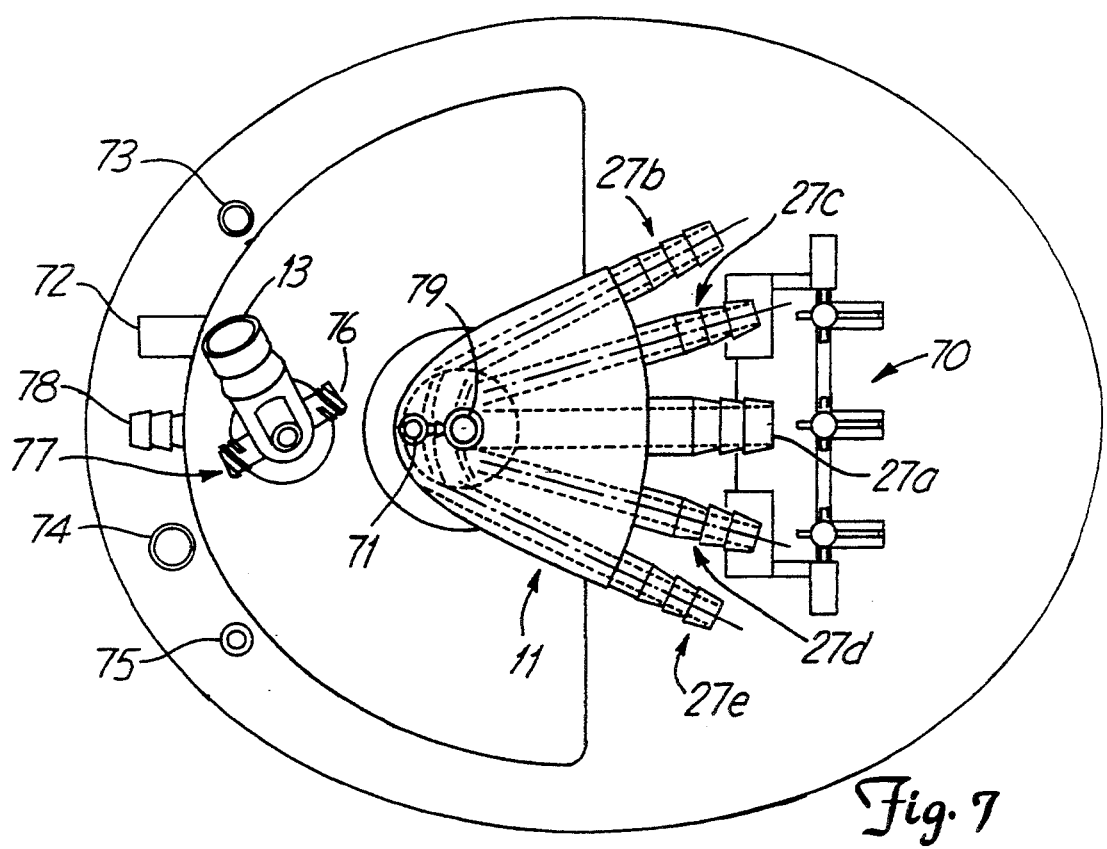
FIG. 7 is a top view of an embodiment of the reservoir of the present invention.

In alternate embodiments of the invention, top 3 may have various fittings and ports in addition to cardiotomy inlet 11 and venous inlet 13. As shown in FIG. 7, top 3 may also include sampling manifold 70, filtered luer 71, vent 72, non-filtered ports 73 and 74, non-filtered luer 75, luer fittings 76 and 77, recirculation port 78, and quick-prime port 79.

In operation, reservoir 1 is connected to an extracorporeal blood circuit. Sucker lines with pumps convey blood to cardiotomy blood inlet 11 which directs the cardiotomy blood into cardiotomy blood filtering and defoaming means 10. The blood then passes through cardiotomy filter element 30. As discussed above, filter element 30 is typically a polyester felt depth filter in order to remove not only gas bubbles that may be entrained in the cardiotomy blood, but also trap any bone or cartilage fragments that may have been drawn into the sucker lines at the surgical site. Cardiotomy filter element 30 is folded up into itself in order to maximize the surface area for the cardiotomy blood to flow through while reducing the total size of filter element 30.

First defoaming element 31 is positioned at the top of cardiotomy blood filtering and defoaming means 10, typically adjacent top 3. Fluid cardiotomy blood flows into filter 30 through lower extension 33 of inlet 11 and does not contact first defoaming element 31. Unless filter 30 becomes clogged, fluid cardiotomy blood flows through filter element 30 and does not contact first defoaming element 31. Blood foam may also be collected from the surgical site or develop within filter element 30. Blood foam will sit on top of the fluid blood, and first defoaming element 31 is positioned so that the blood foam will contact first defoaming element 31, thereby converting the blood foam back into fluid blood. Second defoaming element 32 is also positioned above the normal operating blood level of the reservoir 1.

The cardiotomy blood flows through filter element 30, then flows downward towards filter unit 7. As discussed above, filter unit 7 serves as an additional filter to remove gas bubbles, other emboli, and undesirable macroscopic fragments that are not trapped by filters 10, 12. Filter unit 7 extends from top 3 to bottom 4 and from opposed sidewalls, so that all blood must pass through filter unit 7 as the blood passes from inlet chamber 8 to outlet chamber 9.

Venous blood is drawn from the patient and passes into venous inlet 13. Generally, venous blood is free of particulate matter, such as the cartilage or bone fragments found in cardiotomy blood, but may have gas bubbles or blood clot emboli entrained in the blood. The venous blood flows from inlet 13 into inlet tube 53 which carries the blood toward bottom 4 so that the venous blood does not splash, which can damage the blood or allow gas bubbles to form in the blood. Venous blood then flows through apertures 57 of support means 52 and through filter element 51.

Venous blood filtering and defoaming means 12 also includes a venous defoaming element 54 similar to the first defoaming element in cardiotomy blood filtering and defoaming means 10. Venous defoaming element 54 is positioned adjacent to the top of venous blood filtering and defoaming means 12, above the normal operating blood level of the reservoir. Therefore, in normal operating conditions, fluid venous blood does not contact venous defoaming element 54, but venous blood foam sitting on top of the fluid venous blood contacts venous defoaming element 54, converting the blood foam to fluid blood.

Aperture 58 of stand 55 is positioned on the downstream side of ledge 21 so that venous blood exiting aperture 58 will flow downward toward filter unit 7. Venous blood filtering and defoaming means 12 is also positioned in inlet chamber 8 to reduce areas where blood may stagnate. Again, venous blood exiting venous filter element 12 flows downward through filter unit 7.

The combined cardiotomy and venous blood flowing through filter unit 7 must flow either over top surface 61 or lateral surface 62 of displacement means 60. Again, this configuration serves to create a uniform blood flow in outlet chamber 9, as well as reduce vortices forming in the blood near outlet 14.

Figure 8:
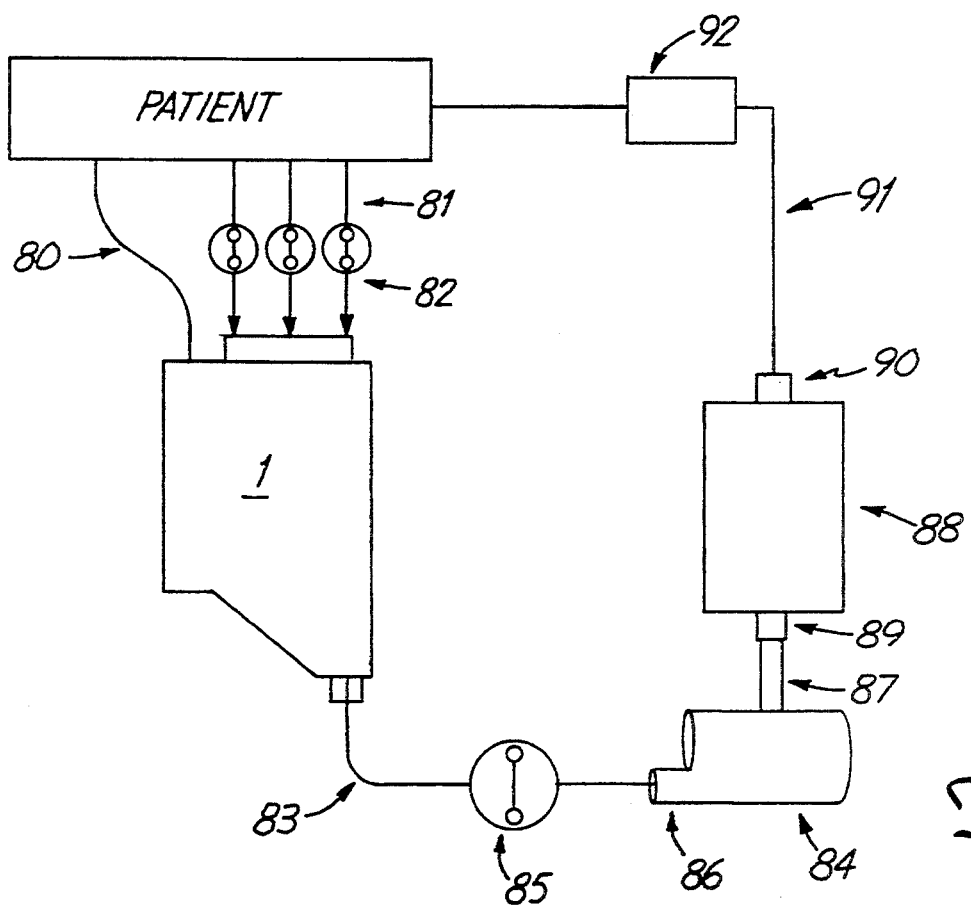
FIG. 8 is a schematic diagram of an extracorporeal blood circuit incorporating the reservoir of the present invention.

As shown in the schematic diagram of FIG. 8, reservoir 1 may be used in an extracorporeal blood bypass circuit, e.g., a bypass circuit for open-heart surgery. Such a circuit includes a venous line 80 to blood reservoir 1. Venous blood flows by gravity from the patient to blood reservoir 1. Also, cardiotomy blood may be pumped from the surgical site of the patient by cardiotomy lines 81 and pumps 82 connected to reservoir 1. Line 83 conveys blood from combined venous and cardiotomy blood reservoir 1 to heat exchanger 84, via blood pump 85. Heat exchanger 84 regulates the temperature of the blood and includes heat exchanger inlet 86 and heat exchanger outlet 87. Blood oxygenator 88 is directly connected to heat exchanger 84. Blood oxygenator 88 regulates the oxygen and carbon dioxide content of blood, and includes oxygenator blood inlet 89 and oxygenator blood outlet 90. The blood then flows from oxygenator 88 through line 91 back to the patient. Line 91 may also include arterial filter 92.

The above description and accompanying drawings are provided for the purpose of describing embodiments of the invention and are not intended to limit the scope of the invention in any way.

I claim:

1. A combined venous and cardiotomy blood reservoir, comprising:
    (a) a rigid shell having a top, a bottom, and a continuous sidewall, said top and bottom connected to the sidewall to form an enclosed reservoir;
    (b) a filter unit having two faces and four sides, said filter unit disposed within the reservoir where two of the sides are opposed and connected to the sidewall and the other two of the sides are opposed and connected, respectively, to the top and bottom, said filter unit dividing the enclosed reservoir into an enclosed inlet chamber and an enclosed outlet chamber, said inlet chamber and outlet chamber in fluid communication through said filter unit;
    (c) a cardiotomy blood filter and defoamer located within the inlet chamber and extending substantially from the top to the bottom of the shell, and a cardiotomy blood inlet in fluid communication with the cardiotomy blood filter and defoamer;
    (d) a venous blood filter and defoamer located within the inlet chamber separate of the cardiotomy blood filter and defoamer and extending substantially from the top to the bottom of the shell, and a venous blood inlet in fluid communication with the venous blood filter and defoamer;
    (e) a blood outlet in fluid communication with the outlet chamber.

2. The blood reservoir of claim 1 wherein the sidewall is tapered from the top to the bottom.

3. The blood reservoir of claim 1 wherein the sidewall is elliptical.

4. The blood reservoir of claim 1 wherein the filter unit comprises a filter element and means for supporting the filter element.

5. The blood reservoir of claim 4 wherein the filter element is a screen filter.

6. The blood reservoir of claim 5 wherein the screen filter is a polyester screen having a pore size within the range of 100 to 200 microns.

7. The blood reservoir of claim 1 wherein the cardiotomy blood filter and defoamer comprises a cardiotomy filter element having a top and a bottom, said cardiotomy filter element extending substantially from the top to the bottom of the shell, and a first defoaming element extending from the top of the cardiotomy filter element partially towards the bottom of the cardiotomy filter element and being surrounded by the cardiotomy filter element.

8. The blood reservoir of claim 7 wherein the cardiotomy blood filter and defoamer further comprises a second defoaming element extending from the top of the cardiotomy filter element partially towards the bottom of the cardiotomy filter element and surrounding the cardiotomy filter element.

9. The blood reservoir of claim 8 wherein the first defoaming element comprises thermally reticulated polyurethane foam having a pore size within the range of 5 to 50 ppi, and coated with an antifoam agent.

10. The blood reservoir of claim 7 wherein the cardiotomy filter element is a depth filter.

11. The blood reservoir of claim 10 wherein the depth filter is a polyester felt filter having a mean pore the size in the range of 20 to 50 microns.

12. The blood reservoir of claim 7 wherein the second defoaming element comprises a thermally reticulated polyurethane foam having a pore size within the range of 5 to 50 ppi.

13. The blood reservoir of claim 1 wherein the venous filter and defoamer comprises a cylindrical venous filter element extending substantially from the top to the bottom of the shell and a filter support.

14. The blood reservoir of claim 13 wherein the venous filter element is a polyester screen having a pore size within the range of 50 to 250 microns.

15. The blood reservoir of claim 13 wherein said venous filter and defoamer further comprises a third defoaming element extending substantially from the top of the shell partially toward the bottom of the shell and surrounded by said cylindrical venous filter element.

16. The blood reservoir of claim 15 wherein said third defoaming element comprises thermally reticulated polyurethane foam having a pore size within the range of 5 to 50 ppi, and coated with an antifoam agent.

17. The blood reservoir of claim 13 wherein the filter support comprises a cylindrical web frame having a plurality of apertures, said frame surrounded by said venous filter element.

18. The blood reservoir of claim 1 wherein the combined venous and cardiotomy blood reservoir further comprises a displacement member disposed within the outlet chamber.

19. The blood reservoir of claim 1 wherein a substantial portion of the bottom of the shell slopes away from the top, and the outlet is located at the portion of the bottom furthest from the top.

20. The blood reservoir of claim 1 wherein said cardiotomy blood inlet is located on the top of the shell.

21. The blood reservoir of claim 1 wherein said cardiotomy blood inlet is located on the sidewall of the shell adjacent to the top.

22. The blood reservoir of claim 1 wherein said cardiotomy blood inlet is rotatable.

23. The blood reservoir of claim 1 wherein said venous blood inlet is located on the top of the shell.

24. The blood reservoir of claim 1 wherein said venous blood inlet is located on the sidewall of the shell adjacent to the top.

25. The blood reservoir of claim 1 wherein said venous blood inlet is rotatable.

26. An extracorporeal blood circuit, comprising:
    (a) a combined venous and cardiotomy blood reservoir;
    (b) a heat exchanger for regulating the temperature of blood comprising a heat exchanger inlet and heat exchanger outlet, said heat exchanger in fluid communication with said combined venous and cardiotomy blood reservoir; and
    (c) a blood oxygenator for regulating the oxygen and carbon dioxide content of blood, comprising an oxygenator blood inlet and an oxygenator blood outlet, said oxygenator in fluid communication with said heat exchanger;
    (d) wherein said combined venous and cardiotomy blood reservoir comprises,
        (i) a rigid shell having a top, a bottom, and a continuous sidewall, said top and bottom connected to the sidewall to form an enclosed reservoir,
        (ii) a filter unit having two faces and four sides, said filter unit disposed within the reservoir where two of the sides are opposed and connected to the sidewall and the other two of the sides are opposed and connected, respectively, to the top and bottom, said filter unit dividing the enclosed reservoir into an enclosed inlet chamber and an enclosed outlet chamber, said inlet chamber and outlet chamber in fluid communication through said filter unit,
        (iii) a cardiotomy blood filter and defoamer located within the inlet chamber and extending substantially from the top to the bottom of the shell, and a cardiotomy blood inlet in fluid communication with the cardiotomy blood filter and defoamer,
        (iv) a venous blood filter and defoamer located within the inlet chamber separate of the cardiotomy blood filter and defoamer and extending substantially from the top to the bottom of the shell, and a venous blood inlet in fluid communication with the venous blood filter and defoamer, and
        (v) a blood outlet in fluid communication with the outlet chamber.

* * * * *

UNITED STATES PATENT AND TRADEMARK OFFICE
CERTIFICATE OF CORRECTION

PATENT NO. : 5,411,705
DATED : May 2, 1995
INVENTOR(S) : Thor et al.

It is certified that error appears in the above-indentified patent and that said Letters Patent is hereby corrected as shown below:

Column 7, line 29, replace "robe" with --tube--.

Signed and Sealed this

Nineteenth Day of August, 1997

Attest:

BRUCE LEHMAN

Attesting Officer

Commissioner of Patents and Trademarks